United States Patent
Hansen et al.

(10) Patent No.: US 10,675,589 B2
(45) Date of Patent: Jun. 9, 2020

(54) CLEANING OF WATER FILTRATION MEMBRANES

(71) Applicant: Novozymes A/S, Bagsvaerd (DK)

(72) Inventors: Rasmus Rune Hansen, Bagsvaerd (DK); Ethan Baker, Roanoke, VA (US)

(73) Assignee: Novozymes A/S, Bagsvaerd (DK)

( * ) Notice: Subject to any disclaimer, the term of this patent is extended or adjusted under 35 U.S.C. 154(b) by 74 days.

(21) Appl. No.: 15/768,466

(22) PCT Filed: Oct. 14, 2016

(86) PCT No.: PCT/US2016/056955
§ 371 (c)(1),
(2) Date: Apr. 13, 2018

(87) PCT Pub. No.: WO2017/066510
PCT Pub. Date: Apr. 20, 2017

(65) Prior Publication Data
US 2018/0296981 A1    Oct. 18, 2018

Related U.S. Application Data

(60) Provisional application No. 62/241,959, filed on Oct. 15, 2015.

(30) Foreign Application Priority Data

Oct. 14, 2015 (EP) .................................... 15189864

(51) Int. Cl.
| | | |
|---|---|---|
| *B01D 65/02* | (2006.01) | |
| *C12N 9/22* | (2006.01) | |
| *B01D 65/08* | (2006.01) | |
| *B01D 61/18* | (2006.01) | |
| *B01D 61/22* | (2006.01) | |
| *C11D 3/386* | (2006.01) | |

(52) U.S. Cl.
CPC ........... *B01D 65/022* (2013.01); *B01D 61/18* (2013.01); *B01D 61/22* (2013.01); *B01D 65/02* (2013.01); *B01D 65/08* (2013.01); *C11D 3/386* (2013.01); *C12N 9/22* (2013.01); *B01D 2321/166* (2013.01); *B01D 2321/185* (2013.01); *C02F 2303/16* (2013.01); *C02F 2303/20* (2013.01)

(58) Field of Classification Search
None
See application file for complete search history.

(56) References Cited

U.S. PATENT DOCUMENTS

| | | | | |
|---|---|---|---|---|
| 6,555,055 | B1 * | 4/2003 | Cisar | A61C 1/0076 |
| | | | | 134/102.1 |
| 9,675,736 | B2 * | 6/2017 | Burgess | A61L 29/16 |
| 2002/0061312 | A1 * | 5/2002 | Medzhitov | A61K 39/385 |
| | | | | 424/192.1 |
| 2009/0314713 | A1 * | 12/2009 | Shelby | B01D 63/10 |
| | | | | 210/636 |
| 2011/0120921 | A1 * | 5/2011 | Kim | B67D 1/0004 |
| | | | | 210/97 |
| 2018/0334402 | A1 * | 11/2018 | Williams | B01D 35/147 |

FOREIGN PATENT DOCUMENTS

| | | |
|---|---|---|
| WO | 1997002753 A1 | 1/1997 |
| WO | 2006031554 A2 | 3/2006 |
| WO | 2009061380 A2 | 5/2009 |
| WO | 2011098579 A1 | 8/2011 |
| WO | 2014087011 A1 | 6/2014 |

OTHER PUBLICATIONS

Nijland et al, 2010, PLOS One, Public library of Science 5(12), e15668.
Tetz et al, 2009, Antimic Agents Chemoth 53(3), 1204-1209.

* cited by examiner

*Primary Examiner* — Chester T Barry
(74) *Attorney, Agent, or Firm* — Adam Rucker

(57) ABSTRACT

Methods for cleaning water filtration membranes by treatment with a DNase containing cleaning composition. Optionally the composition also comprises a biocidal and/or other enzymes such as proteases. The DNAse may be derived from *Aspergillus oryzae* or from *Bacillus licheniformis*.

16 Claims, No Drawings
Specification includes a Sequence Listing.

SEQUENCE LISTING

<160> NUMBER OF SEQ ID NOS: 2

<210> SEQ ID NO 1
<211> LENGTH: 206
<212> TYPE: PRT
<213> ORGANISM: Aspergillus oryzae

<400> SEQUENCE: 1

```
Ala Leu Lys Thr Gly Ser Gly Asp Ser Gln Ser Asp Pro Ile Lys Ala
1               5                   10                  15
Asp Leu Glu Val Lys Gly Gln Ser Ala Leu Pro Phe Asp Val Asp Cys
            20                  25                  30
Trp Ala Ile Leu Cys Lys Gly Ala Pro Asn Val Leu Gln Arg Val Asn
        35                  40                  45
Glu Lys Thr Lys Asn Ser Asn Arg Asp Arg Ser Gly Ala Asn Lys Gly
    50                  55                  60
Pro Phe Lys Asp Pro Gln Lys Trp Gly Ile Lys Ala Leu Pro Pro Lys
65                  70                  75                  80
Asn Pro Ser Trp Ser Ala Gln Asp Phe Lys Ser Pro Glu Glu Tyr Ala
                85                  90                  95
Phe Ala Ser Ser Leu Gln Gly Gly Thr Asn Ala Ile Leu Ala Pro Val
            100                 105                 110
Asn Leu Ala Ser Gln Asn Ser Gln Gly Gly Val Leu Asn Gly Phe Tyr
        115                 120                 125
Ser Ala Asn Lys Val Ala Gln Phe Asp Pro Ser Lys Pro Gln Gln Thr
    130                 135                 140
Lys Gly Thr Trp Phe Gln Ile Thr Lys Phe Thr Gly Ala Ala Gly Pro
145                 150                 155                 160
Tyr Cys Lys Ala Leu Gly Ser Asn Asp Lys Ser Val Cys Asp Lys Asn
                165                 170                 175
Lys Asn Ile Ala Gly Asp Trp Gly Phe Asp Pro Ala Lys Trp Ala Tyr
            180                 185                 190
Gln Tyr Asp Glu Lys Asn Asn Lys Phe Asn Tyr Val Gly Lys
        195                 200                 205
```

<210> SEQ ID NO 2
<211> LENGTH: 109
<212> TYPE: PRT
<213> ORGANISM: Bacillus licheniformis

<400> SEQUENCE: 2

```
Ala Arg Tyr Asp Asp Ile Leu Tyr Phe Pro Ala Ser Arg Tyr Pro Glu
1               5                   10                  15
```

-continued

```
Thr Gly Ala His Ile Ser Asp Ala Ile Lys Ala Gly His Ser Asp Val
            20              25              30

Cys Thr Ile Glu Arg Ser Gly Ala Asp Lys Arg Arg Gln Glu Ser Leu
        35              40              45

Lys Gly Ile Pro Thr Lys Pro Gly Phe Asp Arg Asp Glu Trp Pro Met
    50              55              60

Ala Met Cys Glu Glu Gly Gly Lys Gly Ala Ser Val Arg Tyr Val Ser
65              70              75              80

Ser Ser Asp Asn Arg Gly Ala Gly Ser Trp Val Gly Asn Arg Leu Ser
            85              90              95

Gly Phe Ala Asp Gly Thr Arg Ile Leu Phe Ile Val Gln
            100             105
```

CLEANING OF WATER FILTRATION MEMBRANES

CROSS-REFERENCE TO RELATED APPLICATIONS

This application is a 35 U.S.C. 371 national application of PCT/US2016/056955, filed Oct. 14, 2016, which claims priority or the benefit under 35 U.S.C. 119 of European application no. 15189864.0, filed Oct. 14, 2015, and U.S. provisional application No. 62/241,959, filed Oct. 15, 2015. The contents of these applications are fully incorporated herein by reference.

FIELD OF THE INVENTION

The present invention relates to cleaning of water filtration membranes using DNase containing cleaning compositions.

BACKGROUND OF THE INVENTION

Membrane fouling is a problem encountered in membrane filtration processes, and it is a major factor in determining their practical application in water and wastewater treatment and desalination in terms of technology and economics. Membrane fouling includes inorganic fouling/scaling, particulate/colloidal fouling, and organic fouling with dead organic matter or live microorganisms, which would typically form a biofilm. Fouling due to organic and inorganic components and microorganisms can occur simultaneously, and these components may interact in terms of mechanism.

A well-known means for cleaning filtration membranes is "cleaning-in-place" (CIP). A typical CIP cycle will often include the use of chemicals for high pH (e.g., NaOH), low pH (e.g., citric acid or nitric acid), water and biocides for disinfection, e.g., bleach. A typical CIP cycle for cleaning membranes used in the dairy industry consists of many steps which often include:

Flush/Pre-rinse with clean water flux, which may be heated up to 60-80° C. and recirculated for a period of time.
Circulation of caustic soda solution (NaOH) at a temperature about 60-80° C. for a period of time.
Intermediate rinsing with clean water flux.
Circulation of acidic solution for a period of time.
Final rinse with clean water flux.
Final air blow.

Similar processes exist for membrane cleaning in other business segment, and the individual steps can be applied in different order dependent on the nature of the membrane fouling. A typical CIP cycle for cleaning membranes used in the enzyme manufacturing industry includes water flush, a cold and hot caustic rinse, and nitric acid rinse.

The use of harsh chemicals in CIP is undesirable and poses a problem to the environment. In the past years CIP methods including the use of enzymes have been developed.

International patent application WO 97/02753 concerns a solution comprising a protease and a lipase for cleaning-in-place. The solution has been found effective in cleaning process equipment containing residues of milk or burnt milk.

Compared to a typical CIP procedure, there are several benefits of improved membrane cleaning by use of DNase enzymes, such as, saving power to pump liquid through less fouled membranes, reducing use of harsh and hazardous chemicals, reducing cost for neutralising acids and bases and discharge after use, extension of membrane lifetime due to milder cleaning conditions and removal of fouling not removed by chemical or physical means.

SUMMARY

The present invention provides a method for cleaning a water filtration membrane by contacting the membrane with a liquid cleaning composition comprising a DNase.

The cleaning process may be Cleaning-In-Place (CIP) or Cleaning-Out-of-Place (COP).

In an embodiment, the water flow rate through the membrane (flux) is improved.

In another embodiment, the method is preceded or followed by contacting the membrane with a biocidal composition.

In yet another embodiment, the water filtration membrane comprises a biofilm, which preferably includes one or more bacteria selected from the group consisting of *Acinetobacter, Bacillus, Comamonas, Escherichia, Pseudomonas,* and *Sphingomonas* species.

Other aspects and embodiments of the invention will be apparent from the description and examples.

DETAILED DESCRIPTION OF THE INVENTION

In the context of the present invention, the terms "water filtration" and "water treatment" include fitration and treatment of aqueous solutions and aqueous suspensions, as well as substantially pure water.

It has been shown that extracellular DNA plays an important role in initiating attachment of biotic and abiotic organic matter to membranes. Extracellular DNA (eDNA) has been released to the environment from dead cells of animal, plant or microbial origin. DNA is sticky and binds to surfaces and other molecules, thereby inducing membrane fouling either by simply aggregating smaller molecules into bigger ones or as initiation of biofilm formation. In addition to the adhesion of microorganisms to surfaces, eDNA also functions as a structural component in a biofilm. The role of eDNA in biofilms varies from one microbial species to the next, and other extracellular polymers like proteins and polysaccharides also play important roles, however it is clear that eDNA plays a major role in microbial attachment to surfaces and early biofilm formation.

Membranes used for filtration/purification of water or non-aqueous liquids include ultrafiltration (UF), microfiltration (MF), nanofiltration (NF) and reverse osmosis (RO) membranes. When the membranes get fouled, in order to maintain a certain flow of liquid through the membrane, the operator has to increase the pressure over the membrane (trans membrane pressure) which results in an increased consumption of power. Above a certain pressure the integrity of the membrane is irreversible damaged.

The use of DNase enzymes for cleaning water filtration membranes can reduce the sticking of organic material and microorganisms to the membrane, whereby the flow of water/liquid through the membrane is improved. Also, the use of a DNase for membrane cleaning can be combined with traditional chemical cleaning agents like acids, bases, bleach and other disinfectants and biocides. The DNase cleaning step can be applied either before or after cleaning procedures with other cleaning chemicals or formulations.

Typically used biocides and cleaning chemicals include 2,2-dibromo-3-nitrilopropionamide (DBNPA), rodalon, sodium hypochlorite, $H_2O_2$, $HNO_3$, citric acid, oxalic acid, NaOH, EDTA, surfactants, coagulants, antiscalants and dispersants.

The membrane cleaning procedure can be either "Cleaning-In-Place" (CIP) or "Cleaning-Out-of-Place" (COP). In a CIP cleaning procedure the membranes remain installed in the treatment facility while subjected to the cleaning formulation either in a soaking procedure wherein the membranes are submerged or soaked in the cleaning formulation or in a flow through procedure wherein the cleaning formulation is continuously circulated through the membrane.

In a COP process the membranes are removed from the facility and cleaned in a separate soaking or flow through procedure.

Dependent on the nature of the fouling, the CIP or COP cleaning procedures can extend for a few minutes to several hours, such as over night.

A typical membrane cleaning procedure can have several separate steps separated by flushing with water. The order of the chemicals and DNase cleaning steps can vary based on the nature of the membrane foulings.

Dependent on the activity profile of the DNase enzyme, the DNase cleaning procedure can take place at either low, neutral or high pH, and low or high temperature. Preferably, the procedure takes place at pH 6-9 and temperature between 30-70° C.

DNase (Deoxyribonuclease)

The term "DNase" means a polypeptide with DNase activity that catalyzes the hydrolytic cleavage of phosphodiester linkages in the DNA backbone, thus degrading DNA. Examples of enzymes exhibiting DNase activity are those covered by enzyme classes EC 3.1.11 to EC 3.1.31, as defined in the recommendations of the Nomenclature Committee of the International Union of Biochemistry and Molecular Biology (IUBMB).

The terms "DNases", "DNase enzymes" and the expression "a polypeptide with DNase activity" are used interchangeably throughout the application. For purposes of the present invention, DNase activity is determined according to the procedure described in the Assay I.

In one aspect, the DNase of the present invention has at least 20%, e.g., at least 40%, at least 50%, at least 60%, at least 70%, at least 80%, at least 90%, at least 95%, or at least 100% of the DNase activity of the DNase having the amino acid sequence of SEQ ID NO: 1.

The DNase used according to the present invention is a mature polypeptide exhibiting DNase activity, which comprises or consists of an amino acid sequence having at least 80% sequence identity to the amino acid sequence shown as SEQ ID NO: 1 or SEQ ID NO: 2.

Preferably, the amino acid sequence of the DNase has at least 85% sequence identity, more preferably at least 90%, more preferably at least 95%, 96%, 97%, 98%, 99%, and most preferably 100% sequence identity to the amino acid sequence of SEQ ID NO: 1 or SEQ ID NO: 2. In an embodiment, the amino acid sequence of the DNase is SEQ ID NO: 1 or SEQ ID NO: 2. In another embodiment, the DNase is a fungal DNase, preferably a filamentous fugal DNase, more preferably an *Aspergillus* DNase, and most preferably an *Aspergillus oryzae* DNase. In another embodiment, the DNase is an *Aspergillus oryzae* DNase or a derivative thereof. In yet another embodiment, the DNase is a DNase as disclosed in International patent application no. PCT/EP2015/057883 (now WO 2015/155350), which is hereby incorporated by reference.

In an embodiment, the number of amino acid substitutions, deletions and/or insertions introduced into the amino acid sequence of SEQ ID NO: 1 or SEQ ID NO: 2 is up to 10, e.g., 1, 2, 3, 4, 5, 6, 7, 8, 9, or 10; or up to 5, e.g., 1, 2, 3, 4, or 5; or up to 2. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for DNase activity to identify amino acid residues that are critical to the activity of the molecule. See also, Hilton et al., 1996, *J. Biol. Chem.* 271: 4699-4708. The active site of the DNase or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

The relatedness between two amino acid sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment).

Biofilm

A biofilm is any group of microorganisms in which cells stick to each other on a surface, such as a fibrous surface, a metallic surface, or any other hard surface. These adherent cells are frequently embedded within a self-produced matrix of extracellular polymeric substance (EPS). Biofilm EPS is a polymeric conglomeration generally composed of extracellular DNA, proteins, and polysaccharides.

Biofilms may form on living or non-living surfaces. The microbial cells growing in a biofilm are physiologically distinct from planktonic cells of the same organism, which, by contrast, are single-cells that may float or swim in a liquid medium. Bacteria living in a biofilm usually have significantly different properties from free-floating bacteria of the same species, as the dense and protected environment of the film allows them to cooperate and interact in various ways. One benefit of this environment is increased resistance to detergents and antibiotics, as the dense extracellular matrix and the outer layer of cells protect the interior of the community.

Typical biofilms comprise one or more bacteria selected from the group consisting of *Acinetobacter, Bacillus, Comamonas, Escherichia, Pseudomonas*, and *Sphingomonas* species; such as one or more bacterial species selected from the group consisting of *Acinetobacter calcoaceticus, Bacillus amyloliquefaciens* SC100, *Bacillus amyloliquefaciens* SC168, *Comamonas denitrificans, Escherichia coli* K-12, *Pseudomonas aeruginosa*, and *Sphingomonas mucosissima*.

Non-DNase Enzyme

The non-DNase enzyme to be optionally combined with the DNase, according to the invention, may be one or more non-DNase enzymes selected from the group consisting of amylase, arabinase, carbohydrase, cellulase, cutinase, galactanase, lipase, mannanase, oxidoreductase (haloperoxidase, laccase, oxidase, peroxidase), pectate lyase, pectinase, perhydrolase, protease, and xylanase.

In general, the properties of the selected enzyme(s) should be compatible with the cleaning conditions (i.e., pH-optimum, compatibility with other enzymatic and non-enzymatic ingredients, etc.), and the enzyme(s) should be present in effective amounts.

Protease

Suitable proteases include those of bacterial, fungal, plant, viral or animal origin, e.g., vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from, e.g., family M4 or other metalloprotease such as those from M5, M7 or M8 families.

The term "subtilases" refers to a sub-group of serine protease according to Siezen et al., 1991, *Protein Engng.* 4: 719-737, and Siezen et al., 1997, *Protein Science* 6: 501-523. Serine proteases are a subgroup of proteases characterized by having a serine in the active site, which forms a covalent adduct with the substrate. The subtilases may be divided into 6 sub-divisions, i.e., the Subtilisin family, the Thermitase family, the Proteinase K family, the Lantibiotic peptidase family, the Kexin family and the Pyrolysin family.

Examples of subtilases are those derived from *Bacillus* such as *Bacillus alkalophilus, B. amyloliquefaciens, Bacillus gibsonii, Bacillus lentus, Bacillus pumilus*, and *Bacillus subtilis* described in; U.S. Pat. No. 7,262,042 and WO 2009/021867, and subtilisin *lentus*, subtilisin Novo, subtilisin Carlsberg, *Bacillus licheniformis*, subtilisin BPN', subtilisin 309, subtilisin 147 and subtilisin 168 described in WO 89/06279 and protease PD138 described in (WO 93/18140). Other useful proteases may be those described in WO 92/17577, WO 01/16285, WO 02/26024 and WO 02/16547. Examples of trypsin-like proteases are trypsin (e.g., of porcine or bovine origin) and the *Fusarium* protease described in WO 89/06270, WO 94/25583 and WO 2005/040372, and the chymotrypsin proteases derived from *Cellumonas* described in WO 2005/052161 and WO 2005/052146.

A further preferred protease is the alkaline protease from *Bacillus lentus* DSM 5483, as described for example in WO 95/23221, and variants thereof which are described in WO 92/21760, WO 95/23221, EP 1921147 and EP 1921148.

Examples of metalloproteases are the neutral metalloprotease as described in WO 2007/044993 (Genencor Int.) such as those derived from *Bacillus amyloliquefaciens*.

Examples of useful proteases are the variants described in: WO 92/19729, WO 96/34946, WO 98/20115, WO 98/20116, WO 99/11768, WO 01/44452, WO 03/006602, WO 2004/03186, WO 2004/041979, WO 2007/006305, WO 2011/036263, WO 2011/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase™, Duralase™, Durazym™, Relase™, Relase™ Ultra, Savinase™, Savinase™ Ultra, Primase™, Polarzyme™, Kannase™, Liquanase™, Liquanase™ Ultra, Ovozyme™, Coronase™, Coronase™ Ultra, Blaze™, Neutrase™, Everlase™ and Esperase™ (Novozymes A/S), those sold under the tradename Maxatase™, Maxacal™, Maxapem™, Purafect™, Purafect Prime™, Purafect MA™, Purafect Ox™, Purafect OxP™, Puramax™, Properase™, FN2™, FN3™, FN4™, Excellase™, Eraser™, Opticlean™ and Optimase™ (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Proteases, but also other types of enzymes, may be used together with protease inhibitors, which are reversible inhibitors of protease activity, e.g., serine protease activity. Preferably, the protease inhibitor is a (reversible) subtilisin protease inhibitor. In particular, the protease inhibitor may be a peptide aldehyde, boric acid, or a boronic acid; or a derivative of any of these.

Suitable boronic acid derivatives are described in U.S. Pat. Nos. 4,963,655, 5,159,060, WO 95/12655, WO 95/29223, WO 92/19707, WO 94/04653, WO 94/04654, U.S. Pat. Nos. 5,442,100, 5,488,157 and 5,472,628.

Suitable peptide aldehydes are described in WO 94/04651, WO 95/25791, WO 98/13458, WO 98/13459, WO 98/13460, WO 98/13461, WO 98/13461, WO 98/13462, WO 2007/141736, WO 2007/145963, WO 2009/118375, WO 2010/055052 and WO 2011/036153. Alternatively, the peptide aldehyde may have the formula as described in WO 2011/036153.

The peptide aldehyde may be converted into a water-soluble hydrosulfite adduct by reaction with sodium bisulfite, as described in textbooks, e.g., March, J. Advanced Organic Chemistry, fourth edition, Wiley-Interscience, US 1992, p 895; and as described in WO 2013/004636.

Lipase/Cutinase

Suitable lipases and cutinases include those of bacterial or fungal origin. Chemically modified or protein engineered mutants are included. Examples include lipase from *Thermomyces*, e.g., from *T. lanuginosus* (previously named *Humicola lanuginosa*) as described in EP 258068 and EP 305216, cutinase from *Humicola*, e.g., *H. insolens* as described in WO 96/13580, a *Pseudomonas* lipase, e.g., from *P. alcaligenes* or *P. pseudoalcaligenes* (EP 218272), *P. cepacia* (EP 331376), *P. stutzeri* (GB 1372034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, Biochemica et Biophysica Acta 1131: 253-360), *B. stearothermophilus* (JP 64/744992) or *B. pumilus* (WO 91/16422), GDSL-type *Streptomyces* lipases (WO 2010/065455), cutinase from *Magnaporthe grisea* (WO 2010/107560), cutinase from *Pseudomonas mendocina* (U.S. Pat. No. 5,389,536), lipase from *Thermobifida fusca* (WO 2011/084412), *Geobacillus stearothermophilus* lipase (WO 2011/084417), lipase from *Bacillus subtilis* (WO 2011/084599), and lipase from *Streptomyces griseus* (WO 2011/150157) and *S. pristinaespiralis* (WO 2012/137147).

Other examples are lipase variants such as those described in WO 92/05249, WO 94/01541, EP 407225, EP 260105, WO 95/35381, WO 96/00292, WO 95/30744, WO 94/25578, WO 95/14783, WO 95/22615, WO 97/04079, WO 97/07202, WO 00/60063, WO 2007/087508 and WO 2009/109500.

Preferred commercially available lipase enzymes include Lipolase™, Lipolase Ultra™, and Lipex™; Lecitase™, Lipolex™; Lipoclean™, Lipoprime™ (Novozymes A/S). Other commercially available lipases include Lumafast (Genencor Int Inc); Lipomax (Gist-Brocades/Genencor Int Inc) and *Bacillus* sp. lipase from Solvay.

Carbohydrase

A carbohydrase is a general term for enzymes that cleave carbohydrates. In general carbohydrases are named after the substrates they act on, for example amylases act on amylase and cellulases act on cellulose. Many carbohydrases have found use in cleaning and laundry applications, such as amylase, cellulase, pectinase, pectate lyase, mannanase, arabinase, galactanase and xylanase, and all these can be applied in the liquid composition.

Amylase

Suitable amylases include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296,839.

Examples of suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/19467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/10355 or variants thereof having 90% sequence identity to SEQ ID NO: 6. Preferred variants of SEQ ID NO: 6 are those having a deletion in positions 181 and 182 and a substitution in position 193. Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:
M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/19467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/23873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476. More preferred variants are those having a deletion in positions 181 and 182 or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 2008/153815, SEQ ID NO: 10 in WO 01/66712 or variants thereof having 90% sequence identity to SEQ ID NO: 2 of WO 2008/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 2009/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions: N128C+K178L+T182G+Y305R+G475K; N128C+K178L+T182G+F202Y+Y305R+D319T+G475K; S125A+N128C+K178L+T182G+Y305R+G475K; or S125A+N128C+T131I+T165I+K178L+T182G+Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO 01/66712 or a variant having at least 90% sequence identity to SEQ ID NO: 12. Preferred amylase variants are those having a substitution, a deletion or an insertion in one of more of the following positions of SEQ ID NO: 12 in WO 01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particularly preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO 2011/098531, WO 2013/001078 and WO 2013/001087.

Commercially available amylases are Stainzyme™, Stainzyme Plus™, Amplify™, Resilience™, Everest™, Duramyl™, Termamyl™, Termamyl Ultra™; Natalase™, Fungamyl™ and BAN™ (Novozymes A/S), Rapidase™ and Purastar™/Effectenz™, Powerase™ and Preferenz S100 (from Genencor International Inc./DuPont).

Lyases

The lyase may be a pectate lyase derived from *Bacillus*, particularly *B. agaradhaerens* or *B. licherniformis*, or a variant derived of any of these, e.g., as described in U.S. Pat. No. 6,124,127, WO 99/27083, WO 99/07084, WO 02/06442, WO 02/092741, WO 03/095638, Commercially available pectate lyases are XPect™, Pectawash™, and Pectaway™ (Novozymes A/S).

Mannanase

The mannanase may be an alkaline mannanase of Family 5 or 26. It belongs It may be a wild-type from *Bacillus* or *Humicola*, particularly *B. agaradhaerens, B. clausii, B. halodurans, B. licheniformis*, or *H. insolens*. Suitable mannanases are described in WO 99/64619. A commercially available mannanase is Mannaway™ (Novozymes A/S).

Cellulase

Suitable cellulases may be of bacterial or fungal origin. Chemically or genetically modified mutants are included. Suitable cellulases include cellulases from the genera *Acremonium, Bacillus, Fusarium, Humicola, Pseudomonas, Thielavia*, e.g., the fungal cellulases produced from *Fusarium oxysporum, Humicola insolens*, and *Mycelio-phthora thermophila* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/01544.

Commercially available cellulases include Carezyme™, Celluzyme™, Celluclean™, Celluclast™, Endolase™, Renozyme™, Whitezyme™ (Novozymes A/S); Clazinase™, Puradax, Puradax HA, and Puradax EG (available from Genencor) and KAC-500(B)™ (Kao Corporation).

Peroxidases/Oxidases

Suitable peroxidases are comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

The peroxidases also include a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Alternaria, Botrytis, Caldariomyces*, e.g., *C. fumago, Curvularia*, e.g., *C. verruculosa* and *C. inaequalis, Drechslera*, and *Ulocladium*.

Haloperoxidases have also been isolated from bacteria such as *Pseudomonas*, e.g., *P. pyrrocinia*, and *Streptomyces*, e.g., *S. aureofaciens*.

In a preferred embodiment, the haloperoxidase is derivable from *Curvularia* sp., in particular *Curvularia inaequalis* or *Curvularia verruculosa*, such as *C. inaequalis* CBS 102.42 as described in WO 95/27046; or *C. verruculosa* CBS 147.63 or *C. verruculosa* CBS 444.70 as described in WO 97/04102; *Dendryphiella salina* as described in WO 01/79458; *Drechslera hartlebii* as described in WO 01/79459; *Geniculosporium* sp. as described in WO 01/79460; or *Phaeotrichoconis crotalarie* as described in WO 01/79461.

Suitable oxidases include, in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be derived from plants, bacteria or fungi (including filamentous fungi and yeasts).

Suitable examples from fungi include a laccase derivable from a strain of *Aspergillus, Botrytis, Collybia, Coprinopsis*, e.g., *C. cinerea, C. comatus, C. friesii*, and *C. plicatilis, Coriolus*, e.g., *C. hirsutus* (JP 2238885), *Fomes, Lentinus, Myceliophthora*, e.g., *M. thermophila, Neurospora*, e.g., *N. crassa, Panaeolus*, e.g., *P. papilionaceus, Phlebia*, e.g., *P. radiata* (WO 92/01046), *Pleurotus, Podospora, Polyporus*, e.g., *P. pinsitus, Psathyrella*, e.g., *P. condelleana, Rhizoctonia*, e.g., *R. solani, Schytalidium*, e.g., *S. thermophilum*, or *Trametes*, e.g., *T. villosa* and *T. versicolor*.

Suitable examples from bacteria include a laccase derivable from a strain of *Bacillus*.

A laccase derived from *Coprinopsis* or *Myceliophthora* is preferred; in particular a laccase derived from *Coprinopsis cinerea*, as disclosed in WO 97/08325; or from *Myceliophthora thermophila*, as disclosed in WO 95/33836.

Perhydrolase

Suitable perhydrolases are capable of catalyzing a perhydrolysis reaction that results in the production of a peracid from a carboxylic acid ester (acyl) substrate in the presence of a source of peroxygen (e.g., hydrogen peroxide). While many enzymes perform this reaction at low levels, perhydrolases exhibit a high perhydrolysis:hydrolysis ratio, often greater than 1. Suitable perhydrolases may be of plant, bacterial or fungal origin. Chemically modified or protein engineered mutants are included.

Examples of useful perhydrolases include naturally occurring *Mycobacterium* perhydrolase enzymes, or variants thereof. An exemplary enzyme is derived from *Mycobacterium smegmatis*. Such enzyme, its enzymatic properties, its structure, and variants thereof, are described in WO 2005/056782, WO 2008/063400, US 2008/0145353, and US 2007/0167344.

Water Filtration Membranes

A variety of membrane types and configurations can be used in water or wastewater treatment processes. Types of membrane configurations include capillary tube, tubular, hollow fiber, multi-tube, plat-and-frame/flat sheet, pleated cartridge filter, spiral wound, and ceramic including ceramic disc. Membranes can be made from one or more materials including, for example, chlorinated polyethylene, polyacrylonitrile, polysulfone, polyethersulfone, polyvinylalcohol, cellolose acetate, regenerated cellulose, polyvinylidene difluoride, polyethlysulphone, polyethylene, polypropylene, and ceramic material. Other characteristics of the membranes that can vary based on the application include, for example, the membrane pore size. The size of the membrane pores may be larger or smaller depending upon the size of particulate or impurity being removed from the water or wastewater. Membrane types, according to the present invention, include those utilized for ultrafiltration, microfiltration, and nanofiltration.

Membrane Bioreactor Systems

Membrane bioreactor (MBR) systems typically combine two basic processes: biological degradation and membrane separation, into a single process where suspended solids and microorganisms responsible for biodegradation are separated from the treated water by a membrane filtration unit. See, for example, *Water Treatment Membrane Processes*, McGraw-Hill, 1996, p. 17.2. The entire biomass is confined within the system, providing for both control of the residence time for the microorganisms in the reactor (sludge age) and the disinfection of the effluent.

In a typical MBR unit, influent wastewater is pumped or gravity fed into an aeration tank where it is brought into contact with the biomass which biodegrades organic material in the wastewater. Aeration means such as blowers provide oxygen to the biomass. The resulting mixed liquor is pumped or gravity fed from the aeration tank into the membrane module where it is mechanically or gravitationally filtered through a membrane under pressure or is drawn through a membrane under low vacuum. In some systems, the aeration tank and the membrane tank are the same tank. The effluent is discharged from the system while the concentrated mixed liquor is returned to the bioreactor. Excess sludge is pumped out in order to maintain a constant sludge age, and the membrane is regularly cleaned by backwashing, chemical washing, air scouring, or any combination of these mechanisms.

MBR systems have multiple configurations. Two main MBR process configurations include submerged/immersed and sidestream. There are also two primary mechanisms of hydraulic operation including pumping and airlifting. These configurations and bulk liquid transfer modes are typically referred to as conventional biomass rejection MBRs. Other configurations include extractive and diffusive process modes which employ membranes for purposes other than separating biomass from the treated water. All of these process configurations include one or more membrane units comprising membranes such as those described in the "Membranes" section above.

In one embodiment, the membranes are present in a membrane bioreactor. In another embodiment, the wastewater treatment process occurs in a membrane bioreactor in which the membrane flat-sheet cassette unit, or hollow-fiber unit, itself is typically immersed.

In one embodiment, the wastewater is pretreated prior to entering the membrane bioreactor. Pretreatment can occur at the source of the wastewater, at a pretreatment plant, or as part of the overall MBR system. Such pretreatments can include a bar screen, grit chamber, or rotary drum screen to achieve coarse solids removal. Other pretreatments may include removal of substances such as harmful pollutants, oils or fuels, or other toxic substances.

Water Treatment Processes

One or more water treatment processes are contemplated by the present invention. Such water treatment processes include, but are not limited to, reverse osmosis, water desalination and drinking water purification, and wastewater treatment processes. The water or wastewater, according to the present invention, can be from any source including human waste, cesspit leakage, septic tank discharge, sewage plant discharge, washing water such as greywater or sullage, collected rainwater, groundwater, surplus manufactured liquids, seawater, river water, manmade liquid disposal, highway drainage, storm drains, blackwater, process water from industries manufacturing products including electronics, transportation vehicles, pharmaceuticals, paints, lubricants, plastics, crude oil and gas, and thereof derived refined products, feed, food and beverages, textile, non-wowens, paper and pulp, processed grains and vegetable oils, chemicals, proteins (e.g., enzymes), industrial waste, industrial site wastewater or drainage such as cooling or process waters, and agricultural wastewater or drainage.

Liquid Cleaning Composition

The liquid cleaning composition used according to the invention has a physical form, which is not solid (or gas). It may be a pourable liquid, a pourable gel or a non-pourable gel. It may be either isotropic or structured, preferably isotropic.

The liquid cleaning composition may be aqueous, typically containing at least 20% by weight and up to 95% water, such as up to 70% water, up to 50% water, up to 40% water, up to 30% water, or up to 20% water. Other types of liquids, including without limitation, alkanols, amines, diols, ethers and polyols may be included in an aqueous liquid composition. An aqueous liquid composition may contain from 0-30% organic solvent. A liquid composition may even be non-aqueous, wherein the water content is below 10%, preferably below 5%.

The cleaning composition may take the form of a unit dose product. A unit dose product is the packaging of a single dose in a non-reusable container. It is increasingly used in detergents for laundry and dish wash. A detergent unit dose product is the packaging (e.g., in a pouch made from a water soluble film) of the amount of detergent used for a single wash.

Pouches can be of any form, shape and material which is suitable for holding the composition, e.g., without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be a blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticizers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids (see e.g., US 2009/0011970).

The choice of cleaning components may include the consideration of the type of membrane to be cleaned, the type and/or degree of soiling, the temperature at which cleaning is to take place, and the formulation of the cleaning product. Although components mentioned below are categorized by general header according to a particular functionality, this is not to be construed as a limitation, as a component may comprise additional functionalities as will be appreciated by the skilled artisan.

The choice of additional components is within the skill of the artisan and includes conventional ingredients, including the exemplary non-limiting components set forth below.
Surfactants The cleaning composition may comprise one or more surfactants, which may be anionic and/or cationic and/or non-ionic and/or semi-polar and/or zwitterionic, or a mixture thereof. In a particular embodiment, the composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in cleaning compositions may be utilized.

When included therein the cleaning composition will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the cleaning composition will usually contain from about 0.1% to about 10% by weight of a cationic surfactant. Non-limiting examples of cationic surfactants include alklydimethylethanolamine quat (AD-MEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein the cleaning composition will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the cleaning composition will usually contain from about 0.1% to about 20% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the cleaning composition will usually contain from about 0.1% to about 10% by weight of a zwitterionic surfactant. Non-limiting examples of zwitterionic surfactants include betaine, alkyldimethylbetaine, sulfobetaine, and combinations thereof.

Methods of Use

As described in the above paragraphs, the present invention provides a method for cleaning a water filtration membrane by contacting the membrane with a liquid cleaning composition comprising a DNase. Preferably, the water flow rate through the membrane (flux) is improved. The liquid cleaning composition may further include the ingredients as described in the paragraphs above.

In an embodiment, the cleaning process is Cleaning-In-Place (CIP) or Cleaning-Out-of-Place (COP).

In an embodiment, the DNase treatment of the water filtration membrane is preceded or followed by contacting the membrane with a biocidal composition.

In an embodiment, the water filtration membrane comprises a biofilm. Preferably, the biofilm comprises one or more bacteria selected from the group consisting of *Acinetobacter, Bacillus, Comamonas, Escherichia, Pseudomonas*, and *Sphingomonas* species. More preferably, the biofilm comprises one or more bacteria selected from the group consisting of *Acinetobacter calcoaceticus, Bacillus amyloliquefaciens* SC100, *Bacillus amyloliquefaciens* SC168, *Comamonas denitrificans, Escherichia coli* K-12, *Pseudomonas aeruginosa*, and *Sphingomonas mucosissima*; preferably the bacteria are *Pseudomonas aeruginosa*.

In another embodiment, the pH of the cleaning composition is 6-9; preferably the pH is about neutral.

In an embodiment, the membrane is contacted with the cleaning composition at a temperature between 30-100° C., preferably at a temperature between 50-80° C.

In yet another embodiment, the membrane is simultaneously or separately contacted with one or more non-DNase enzyme(s) selected from the group consisting of protease, lipase, cutinase, amylase, carbohydrase, cellulase, pectinase, pectate lyase, mannanase, arabinase, galactanase, xylanase, perhydrolase, and oxidoreductase; preferably the non-DNase enzyme is a protease.

In an embodiment, the DNase used in the cleaning composition is an *Aspergillus oryzae* DNase or a derivative thereof. Preferably, the DNase is a polypeptide having DNase activity, which comprises or consists of an amino acid sequence having at least 80% sequence identity to the amino acid sequence shown as SEQ ID NO: 1. More preferably, the DNase is a polypeptide having DNase activity, which comprises or consists of the amino acid sequence shown as SEQ ID NO: 1.

In another embodiment, the DNase is a *Bacillus licheniformis* DNase or a derivative thereof. Preferably, the DNase is a polypeptide having DNase activity, which comprises or consists of an amino acid sequence having at least 80% sequence identity to the amino acid sequence shown as SEQ ID NO: 2.

Assay I: DNase Activity

DNase activity was determined on DNase Test Agar with Methyl Green (BD, Franklin Lakes, N.J., USA), which was prepared according to the manual from supplier. Briefly, 21 g of the DNase Test Agar was dissolved in 500 ml water and then autoclaved for 15 min at 121° C. Autoclaved agar was temperated to 48° C. in water bath, and 20 ml of agar was poured into petridishes with and allowed to solidify by incubation o/n at room temperature. On solidified agar plates, 5 µl of enzyme solutions are added, and DNase activity are observed as colorless zones around the spotted enzyme solutions.

EXAMPLES

Chemicals used as buffers and substrates were commercial products of at least reagent grade. The DNase used in Example 1 was obtained from *Aspergillus oryzae* and is the mature polypeptide of the amino acid sequence shown in SEQ ID NO: 1.

Example 1

Treatment of Water Filtration Membranes with DNase

Bacteria and Culture Media

Seven microbes commonly found in wastewater and water treatment facilities were used to create a multispecies biofilm for this study. The following microbes were chosen:

*Pseudomonas aeruginosa* (ATCC 19429)
*Acinetobacter calcoaceticus* (ATCC 23055)
*Comamonas denitrificans* (ATCC 700937)
*Escherichia coli* K-12 (ATCC 10798)
*Sphingomonas mucosissima* (NRRL B-59454)
*Bacillus amyloliquefaciens* SC100
*Bacillus amyloliquefaciens* SC168

The bacteria were cultivated in Luria Broth (LB; 15.5 g/L; Beckton Dickenson, Franklin Lakes, N.J.) at 30° C. at 200 RPM overnight for the biofilm assays performed. All biofilm assays were performed with LB.

Filter Plate Flux Assay Calibration Curve

To assess flux changes, an indicator dye, Brilliant Green (Clariant Corp, Switzerland), was used to determine the volume of liquid able to pass through the membranes of an EMD Millipore MultiScreen$_{HTS}$ 96-Well Filter Plate. A calibration curve was established for Brilliant Green at a 0.05% (wt/vol) concentration in distilled water. A Costar® 96-well black assay plate with a clear flat bottom was inoculated with volumes of 0.05% Brilliant Green dye ranging from 10-240 µL. These volume series were run in triplicate and measured on the Biotek Synergy H4 Hybrid Reader Kinetic Plate Reader (KPR) at an absorbance at 610 nm. Based on the absorbance readings from each of the corresponding volumes, a standard curve was created in excel by plotting the absorbance vs. the volume corresponding to that absorbance reading. This standard curve generated a linear equation that was used to assess the volume of liquid able to pass through the membranes of the filter plate.

96-Well Filter Plate Flux Assay

Cultures were grown separately overnight in LB at 30° C., shaking at 200 RPM. Culture growth was measured by optical density at 600 nm using a Thermo Scientific Spectronic 20D+ spectrophotometer. Each of the cultures was diluted to an OD 600 of 0.5. Diluted cultures were added together in equal 1 mL volumes in a separate tube and gently vortexed. An EMD Millipore MultiScreen$_{HTS}$ 96-Well Filter Plate was loaded with the mixed cultures. A multi-channel pipette dispensed 100 µL aliquots of the mixed culture into columns 1-4 and 9-12. An LB media control was added in 100 µL aliquots to columns 5-8. Once the plate was set-up, a "breathe-easy" film was applied to the plate. The plate was taped inside a Tupperware container along with a damp WYPALL towel to maintain 99% relative humidity to ensure the plate did not dry out. The Tupperware was placed on a shaker at 200 RPM for 7 days at 30° C.

After the 7 day incubation of the 96-well filter plate, the "breathe-easy" film was removed in the BSL II hood. The plate was inverted over a WYPALL towel, allowing the majority of the liquid in the wells to be removed. Each well was washed with 200 µL of phosphate buffer. The plate was immediately inverted and the buffer was removed from the wells of the plate. To ensure all of the liquid was removed from the wells, the inverted plate was gently tapped on the towel.

From here, the following paths were taken to determine the effectiveness of DNase treatment on bio-fouled membranes:

Effect of Temperature

An ultrafiltrate DNase sample was diluted to a final concentration of 1 ppm in sterile water on the tested plates, with treated wells being chosen semi-randomly. Sterile water was added to wells not receiving DNase treatment. Two plates were incubated at respectively room temperature (22° C.) and optimum temperature (60° C.) for one hour. After incubation, the plates were inverted and the liquid was removed from the wells. The plates were rinsed once again with phosphate buffer and the liquid was removed.

Effect of Enzyme Concentration

An ultrafiltrate DNase sample was diluted to a final concentration of respectively 0.1 ppm and 1 ppm in sterile water on two separate plated plates, with treated wells being chosen semi-randomly. Sterile water was added to wells not receiving DNase treatment. The two plates were incubated at room temperature (22° C.) for 20 minutes. After incubation, the plates were inverted and the liquid was removed from the wells. The plates were rinsed once again with phosphate buffer and the liquid was removed.

Effect of Time

An ultrafiltrate DNase sample was diluted to a final concentration of 1 ppm in sterile water on the tested plates, with treated wells being chosen semi-randomly. Sterile water was added to wells not receiving DNase treatment. Five plates were incubated at room temperature (22° C.) for respectively 0, 5, 10, 20 and 60 minutes. After incubation, the plates were inverted and the liquid was removed from the wells. The plates were rinsed once again with phosphate buffer and the liquid was removed.

Once each of the plates was rinsed with phosphate buffer, a 200 μL sample of 0.05% Brilliant Green indicator dye was added to each well. The filter plate was placed over a Costar® 96-well black with a clear flat bottom and used as a collection plate. This combination was placed in an Eppendorf Centrifuge 5810 along with a blank counter-balance. The centrifuge was set for one minute at 150 rcf at room temperature (22° C.). After centrifugation, the collection plate was removed from the centrifuge and the volume of the indicator dye that passed through the membranes into each of the respective wells was measured on the Biotek Synergy H4 Hybrid Reader Kinetic Plate Reader (KPR) at an absorbance at 610 nm. Using the equation generated from the calibration curve (described above), a volume could be calculated from each well of the collection plate. Flux percentage was calculated by dividing the treated wells by their corresponding un-fouled controls. This was performed with un-treated fouled wells as well, to show flux comparisons between membranes treated with DNase and those that were not.

96-Well Filter Plate Flux Assay Pre-Treated with DNase

The seven microorganisms previously mentioned were grown separately overnight in LB at 30° C., shaking at 200 RPM. Culture growth was measured by optical density at 600 nm using a Thermo Scientific Spectronic 20D+ spectrophotometer. Each culture was diluted to an OD 600 of 0.5. Diluted cultures were added together in equal 1 mL volumes in a separate tube and gently vortexed. An EMD Millipore MultiScreen$_{HTS}$ 96-Well Filter Plate was loaded with the mixed cultures as well as ultrafiltrate DNase of three species (*Aspergillus oryzae*, *Bacillus licheniformis* and *Bacillus subtilis*) in selected wells. Treated wells were chosen randomly, while sterile water was added to wells not receiving DNase treatment. Once the plate was set-up, a "breathe-easy" film was applied to the plate. The plate was taped inside a Tupperware container along with a damp WYPALL towel to maintain 99% relative humidity to ensure the plate did not dry out. The Tupperware was placed on a shaker at 200 RPM for 7 days at 30° C.

After the 7 day incubation of the 96-well filter plate, the "breathe-easy" film was removed in a BSL II hood. The plate was inverted over a WYPALL towel, allowing all of the liquid in the wells to be removed. Wells were washed with 200 μL of phosphate buffer. The plate was immediately inverted and the buffer was removed from the wells of the plate. To ensure all of the liquid was removed from the wells, the inverted plate was gently tapped on the towel.

Once the filter plates were rinsed with phosphate buffer, 200 μL of 0.05% Brilliant Green indicator dye was added to each well. The filter plate was placed over a Costar® 96-well black with a clear flat bottom assay plate used as a collection plate. This combination was placed in an Eppendorf Centrifuge 5810 along with a blank counter-balance. The centrifuge was set for a minute at 150 rcf at room temperature (22° C.). After centrifugation, the collection plate was removed from the centrifuge and the volume of the indicator dye that passed through the membranes into the collection plate was measured on the Biotek Synergy H4 Hybrid Reader Kinetic Plate Reader (KPR) at an absorbance at 610 nm. The volume passed through each well was calculated using the calibration curve (described above). By dividing the treated wells by their corresponding un-fouled controls, a flux percentage was generated. This was performed with un-treated fouled wells as well, to show flux comparisons between membranes treated with DNase and those that were not.

Results

Effect of Temperature

Temperature showed little effect on DNase efficacy, as DNase treatments administered at room temperature showed very little to no difference in flux compared to the DNase treatments administered at the elevated temperatures. The flux of biofouled membranes treated with DNase was still greater than 88% compared to un-fouled controls (see Table 1).

Effect of Enzyme Concentration

When comparing DNase concentrations of 1 ppm and 0.1 ppm, there was little to no difference between the dosages.

Effect of Time

At each of the timepoints (5 minutes, 10 minutes, 20 minutes, 60 minutes), each of the DNase treatments showed a significant increase in the flux compared to the water treated wells. However, little improvement in flux was noted after the treatment was applied for longer than 20 minutes. At this point in time, the DNase treated membranes reach over 90% of the flux to that of the unfouled membranes (see Table 1).

CONCLUSION

The percent flow through volume passed through membranes of a 96-well filter plate fouled by a multi-species biofilm pre-treated with the ultrafiltrate DNase of *Aspergillus oryzae* at 1 ppm concentrations. Wells treated with the ultrafiltrates showed a significant increase in flux compared to those that went untreated. Flux was restored in fouled membranes to over 88% of the flux of un-fouled membranes.

TABLE 1

Overview of 96-Well filter plate flux assay results.

|  | *Aspergillus oryzae* Ultrafiltrate Flux Volume/Control Volume (Percent Flux) |
|---|---|
| 1 ppm Optimum Temperature | 155.88 μL/169.05 μL (91.7%) |
| Untreated | 120.72 μL/167.69 μL (72.0%) |
| 1 ppm Room Temperature | 155.04 μL/174.03 μL (89.6%) |
| Untreated | 105.52 μL/172.95 μL (61.0%) |
| 0.1 ppm Room Temperature 20 minutes | 150.52 μL/158.59 μL (94.9%) |
| Untreated | 106.3 μL/162.0 μL (65.6%) |
| 1 ppm 5 minutes Room Temperature | 101.08 μL/168.84 μL (59.9%) |
| Untreated | 30.8 μL/169.3 μL (12.3%) |
| 1 ppm 10 minutes Room Temperature | 136.12 μL/170.74 μL (79.7%) |
| Untreated | 45.25 μL/169.20 μL (26.7%) |
| 1 ppm 20 minutes Room Temperature | 152.76 μL/159.26 μL (95.9%) |
| Untreated | 82.82 μL/155.17 μL (53.4%) |
| 1 ppm 60 minutes Room Temperature | 155.04 μL/174.03 μL (89.6%) |
| Untreated | 105.52 μL/172.95 μL (61.0%) |

The invention claimed is:

1. A method for cleaning a water filtration membrane, wherein the water filtration membrane comprises a biofilm, the method comprising
   i) contacting the membrane with a liquid cleaning composition comprising a DNase and one or more non-DNase enzymes selected from arabinose, carbohydrase, cellulase, cutinase, galactanase, lipase, mannanase, oxidoreductase, pectinase, pectate lyase, perhydrolase, protease and xylanase; or
   ii) contacting the membrane with a liquid cleaning composition comprising a DNase, and separately contacting the membrane with one or more non-DNase enzymes selected from amylase, arabinose, carbohydrase, cellulase, cutinase, galactanase, lipase, mannanase, oxidoreductase, pectinase, pectate lyase, perhydrolase, protease and xylanase.

2. The method of claim 1, wherein the cleaning process is Cleaning-In-Place (CIP) or Cleaning-Out-of-Place (COP).

3. The method of claim 1, wherein the water flow rate through the membrane (flux) is improved.

4. The method of claim 1, which is preceded or followed by contacting the membrane with a biocidal composition.

5. The method of claim 1, wherein the biofilm comprises one or more bacteria selected from the group consisting of *Acinetobacter*, *Bacillus*, *Comamonas*, *Escherichia*, *Pseudomonas*, and *Sphingomonas* species.

6. The method of claim 1, wherein the biofilm comprises one or more bacteria selected from the group consisting of *Acinetobacter calcoaceticus*, *Bacillus amyloliquefaciens* SC100, *Bacillus amyloliquefaciens* SC168, *Comamonas denitrificans*, *Escherichia coli* K-12, *Pseudomonas aeruginosa*, and *Sphingomonas mucosissima*.

7. The method of claim 1, wherein the pH of the cleaning composition is 6-9.

8. The method of claim 1, wherein the membrane is contacted with the cleaning composition at a temperature between 30-100° C.

9. The method of claim 1, wherein the DNase is an *Aspergillus oryzae* DNase or a derivative thereof.

10. The method of claim 1, wherein the DNase is a polypeptide having DNase activity, which comprises or consists of an amino acid sequence having at least 80% sequence identity to the amino acid sequence shown as SEQ ID NO: 1.

11. The method of claim 1, wherein the DNase is a polypeptide having DNase activity, which comprises or consists of the amino acid sequence shown as SEQ ID NO: 1.

12. The method of claim 1, wherein the DNase is a *Bacillus licheniformis* DNase or a derivative thereof.

13. The method of claim 1, wherein the DNase is a polypeptide having DNase activity, which comprises or consists of an amino acid sequence having at least 80% sequence identity to the amino acid sequence shown as SEQ ID NO: 2.

14. The method of claim 1, wherein the biofilm comprises *Pseudomonas aeruginosa*.

15. The method of claim 1, wherein the pH of the cleaning composition is about neutral.

16. The method of claim 1, wherein the membrane is contacted with the cleaning composition at a temperature between 50-80° C.

* * * * *